(12) United States Patent
Fargahi

(10) Patent No.: US 10,729,412 B2
(45) Date of Patent: Aug. 4, 2020

(54) RELEASE DEVICE FOR RELEASING A MEDICAL IMPLANT FROM A CATHETER AND CATHETER HAVING A RELEASE DEVICE AND METHOD FOR CLAMPING AN IMPLANT THEREIN

(71) Applicant: Biotronik AG, Buelach (CH)

(72) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 1817 days.

(21) Appl. No.: 13/742,499

(22) Filed: Jan. 16, 2013

(65) Prior Publication Data

US 2013/0218138 A1    Aug. 22, 2013

Related U.S. Application Data

(60) Provisional application No. 61/599,430, filed on Feb. 16, 2012.

(51) Int. Cl.
*A61B 17/00* (2006.01)
*A61F 2/966* (2013.01)

(52) U.S. Cl.
CPC ........ *A61B 17/00234* (2013.01); *A61F 2/966* (2013.01); *A61F 2002/9665* (2013.01)

(58) Field of Classification Search
CPC ............. A61F 2/966; A61F 2002/9665; A61B 17/00234
USPC ................................. 623/1.11–1.12
See application file for complete search history.

(56) References Cited

U.S. PATENT DOCUMENTS

| 5,201,757 A | 4/1993 | Heyn et al. |
| 5,709,703 A * | 1/1998 | Lukic ........................ A61F 2/95 606/198 |
| 6,395,017 B1 | 5/2002 | Dwyer et al. |
| 6,858,034 B1 | 2/2005 | Hijlkema et al. |
| 7,264,632 B2 | 9/2007 | Wright et al. |

(Continued)

FOREIGN PATENT DOCUMENTS

| DE | 102009020012 A1 | 5/2009 |
| EP | 1369098 | 12/2003 |

(Continued)

OTHER PUBLICATIONS

Volker Franz, European Search Report for Application No. 12196723.6, dated Jun. 7, 2017.

*Primary Examiner* — Carl H Layno
*Assistant Examiner* — Dacheng Xie
(74) *Attorney, Agent, or Firm* — Greer, Burns & Crain, Ltd; Steven P. Fallon

(57) ABSTRACT

An embodiment of the invention relates to a release device for releasing a medical implant from an insertion device, in the case of which the implant can be released by way of a relative motion between a first and a second insertion element, comprising a clamping element for clamping the implant in the insertion device, having a proximal end which is distant from a distal end of the insertion device in the state of use, and a distal end which faces the distal end of the insertion device in the state of use, wherein the clamping unit comprises a first component and at least one second component, which clamp the implant there between in the clamped state. The invention further relates to an insertion device comprising such a release device and a method for clamping an implant in an insertion device.

16 Claims, 6 Drawing Sheets

(56) References Cited

U.S. PATENT DOCUMENTS

| | | | |
|---|---|---|---|
| 8,016,869 B2 | 9/2011 | Nikolchev | |
| 2004/0193179 A1 | 9/2004 | Nikolchev | |
| 2004/0267348 A1 | 12/2004 | Gunderson et al. | |
| 2005/0228478 A1 | 10/2005 | Heidner | |
| 2006/0229697 A1 | 10/2006 | Gerdts et al. | |
| 2006/0259120 A1* | 11/2006 | Vongphakdy | A61F 2/95 623/1.11 |
| 2006/0271153 A1 | 11/2006 | Garcia et al. | |
| 2007/0233224 A1 | 10/2007 | Leynov et al. | |
| 2008/0004686 A1 | 1/2008 | Hunt et al. | |
| 2008/0208310 A1 | 8/2008 | McDermott et al. | |
| 2009/0287290 A1 | 11/2009 | Macaulay et al. | |
| 2009/0287292 A1 | 11/2009 | Becking et al. | |
| 2010/0241069 A1* | 9/2010 | Hatten | A61F 2/958 604/96.01 |
| 2011/0190862 A1* | 8/2011 | Bashiri | A61F 2/95 623/1.11 |
| 2012/0172929 A1 | 7/2012 | Shalev | |
| 2013/0131775 A1 | 5/2013 | Hadley et al. | |

FOREIGN PATENT DOCUMENTS

| | | |
|---|---|---|
| EP | 1369098 A1 | 12/2003 |
| WO | 199311825 | 6/1993 |
| WO | 2006052642 | 5/2006 |
| WO | 2011004374 | 1/2011 |
| WO | 2011014814 | 2/2011 |
| WO | 2011014814 A2 | 2/2011 |
| WO | 2011066961 A1 | 6/2011 |

* cited by examiner

RELEASE DEVICE FOR RELEASING A MEDICAL IMPLANT FROM A CATHETER AND CATHETER HAVING A RELEASE DEVICE AND METHOD FOR CLAMPING AN IMPLANT THEREIN

CROSS REFERENCE

The present application claims priority on U.S. Application Ser. No. 61/599,430 filed on Feb. 16, 2012; which application is incorporated herein by reference.

TECHNICAL FIELD

An embodiment of the invention relates to a release device for releasing a medical implant from a catheter and a catheter comprising a release device for releasing a medical implant for implantation in an animal body and/or human body, and a method for clamping an implant in such a catheter according to the preambles of the independent claims.

BACKGROUND

Implants are used often in medical applications for implantation in an animal body and/or human body permanently or at least for an extended period of time to perform replacement functions. Examples would be e.g. cardiac pacemakers, brain pacemakers for Parkinson's patients, cardiac implants, cochlear implants, retinal implants, dental implants, joint replacement implants, vascular prostheses or stents.

Before introduction into the body, implants are connected to catheters and must be fastened in such a way that they can be placed precisely at the application site without complication and can be released in a defined manner. To this end, it is known, for example, to equip the implant with eyes which interact with hooks on the catheter, thereby fastening the implant on the catheter.

SUMMARY

One of the problems addressed by the invention is that of providing a release device with which an implant can be connected to an insertion device easily and in a user-friendly manner, and with which an implant can be released in a highly precise and targeted manner.

A further problem is that of providing a related insertion device.

Yet another problem is that of providing a method for clamping an implant by way of a related release device in an insertion device.

These and other problems are solved according to the invention by the features of the claims and features shown and discussed below. Favorable embodiments and advantages of the invention will become apparent from the claims and the description.

A release device for releasing a medical implant from an insertion device is provided, in the case of which the implant can be released by way of a relative motion between a first and a second insertion element. The release device comprises a clamping unit for clamping the implant in the insertion device, having a proximal end which is distant from a distal end of the insertion device in the state of use, and a distal end which faces the distal end of the insertion device in the state of use, wherein the clamping unit comprises a first component and at least one second component, which, in the clamped state, clamp the implant therebetween.

DESCRIPTION OF THE DRAWINGS

The invention is explained in the following in greater detail, as an example, with reference to embodiments that are depicted in drawings. They show, in a diagrammatic representation.

DETAILED DESCRIPTION

Figure 1:
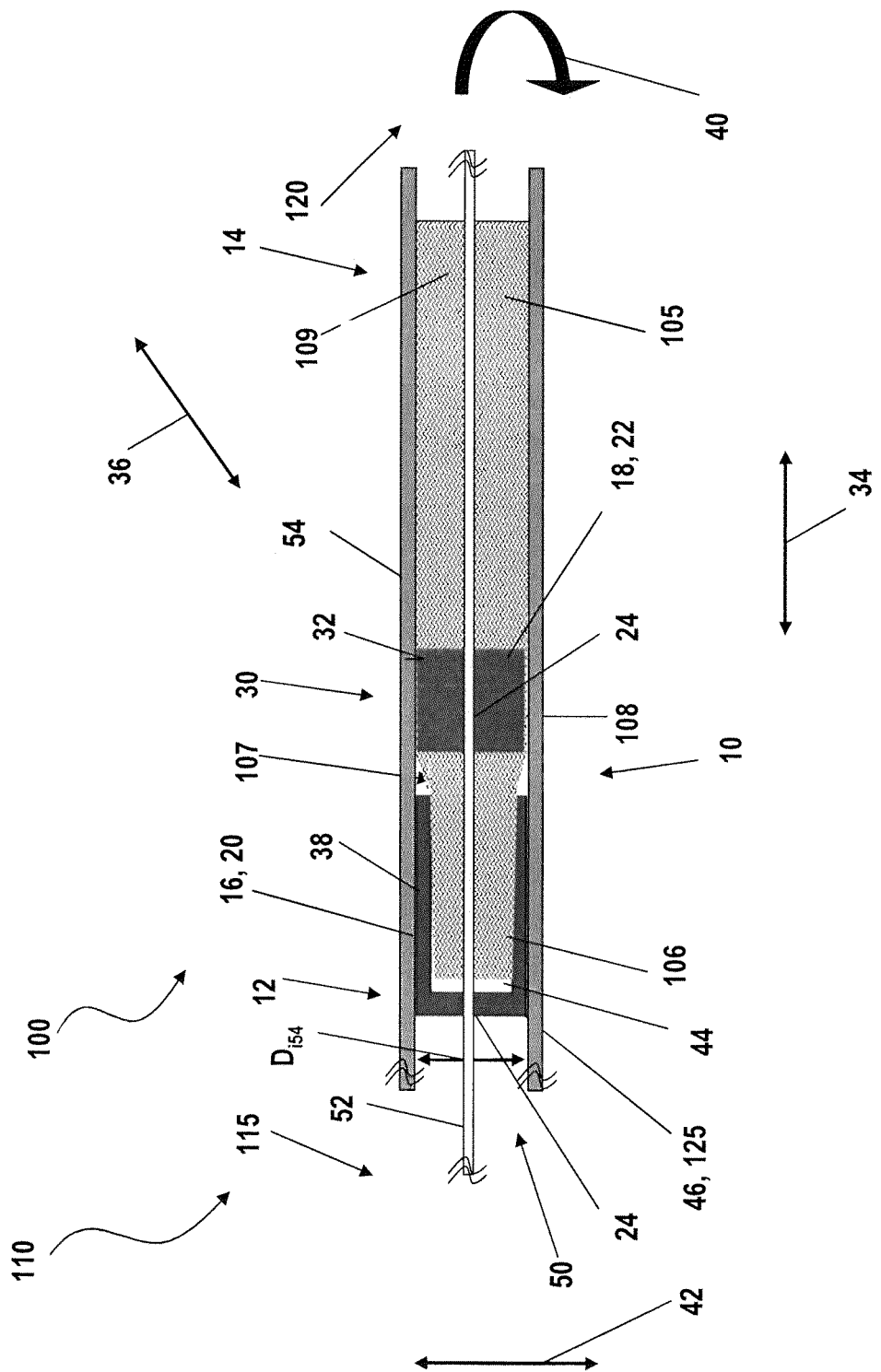
FIG. 1 a longitudinal view of a favorable embodiment of a release device according to the invention comprising an implant placed in an insertion device.

By way of one example embodiment according to the invention, a release device can be provided, in which the implant is securely held or is securely fastened on an insertion element, such as an inner shaft, of the insertion device. The clamping unit furthermore makes it possible to achieve a compact and simple design of the release device. In addition, the release device permits easy handling and installation of the implant on the insertion device, such as a catheter, in the preparation laboratory. Moreover, release of the implant is reliable and rapid. Furthermore, it is possible to eliminate the risk of deformation of the implant and resulting blockage of the release device, which occur with devices according to the prior art, which utilize hooks and eyes.

In this context, a "clamping unit" is intended to broadly refer to a unit which holds another element, in particular the implant, in a defined position on a component of the insertion device, in particular an insertion element or the inner shaft, by way of a clamping effect and/or a frictional connection. The clamping unit itself can provide the clamping effect, or the clamping unit and/or the first and/or the second component can interact with at least one further element, in particular the insertion device, such as an insertion element or the inner shaft and/or an outer shaft of the insertion device. In addition, the clamping unit can have a holding effect which is designed separately from the clamping effect, being provided by way of a material property, for example. In this case, a "clamped state" means a state in which the implant is captively held in the insertion device. The first and the second component apply a force fit to the implant. Furthermore, the first and the second component can have the same design or different designs. In addition, the first and/or the second component is not a component of the implant or is not integrally formed on the implant and/or connected thereto in a bonded manner. Preferably, the components clamp the implant therebetween longitudinally and/or transversely.

Advantageously, in the clamped state, a form-fit connection between the first component and the implant hold the implant in position, thereby preventing the implant from sliding out of the release device or the first component. Furthermore, the implant can also be held captively by way of high friction of a material of the first component. It is advantageous, furthermore, for friction between the at least second component and the implant to hold the implant in position. As a result, it is possible to omit special fastening elements on the clamping unit and/or on the implant, such as hooks and eyes known from the prior art, thereby saving installation space. This interaction between the second component and the implant is preferably supported by an interaction with at least one of the insertion elements and, in particular, the outer shaft, by way of which the implant is securely held.

Preferably, the first component comprises a cavity for accommodating at least one part of the implant, thereby enabling simple interaction between the first component and the implant. It is furthermore provided that the first component comprises at least one sleeve region, thereby enabling the second component to enter into the form-fit connection with the implant by way of a simple design. In this case, a "sleeve region" is intended to mean a portion of the first component, which, in the clamped state, extends along a range of a circumference of the implant and/or encloses it at least partially. The sleeve region of the first component can be a cylinder, for example. It would also be feasible for the first component to be formed by a cylinder. In the installed state of the first component in the insertion device, the sleeve region is preferably disposed on the distal end. In an advantageous embodiment, in the clamped state, the sleeve region of the first component encloses at least a proximal end of the implant, and therefore the first component is disposed toward the user or toward the proximal end of the insertion device. Advantageously, a wall which extends in a radial direction is disposed or, preferably, is integrally formed on the proximal end of the first component, which provides a working surface for a sliding motion of the implant in the insertion device, for example. Furthermore, a proximal end of the first component can also comprise a stopper which serves to limit a motion of the implant in the direction of a proximal end of the insertion device, which would result in blockage of the implant.

In a preferred embodiment, the first component is formed by a socket, thereby making it possible to combine the advantageous features of the cylinder, the wall and the stopper in one component. The at least second component preferably has a cylindrical contour and, in particular, is designed substantially as a solid cylinder, wherein "substantially" is intended to mean that more than 50% of the cylinder, preferably more than 65% and particularly preferably more than 75% is solid. The solid design results in a particularly stable component. Furthermore, the at least second component is formed by a plug connector, thereby ensuring interaction with other components by way of a simple design. In this case, a "plug connector" is intended to broadly mean a component which can be disposed in another component such as a cylinder and/or a socket.

In an advantageous embodiment, the at least second component comprises a material having high static friction in order to hold the implant in position in the clamped state, thereby enabling the implant to be affixed using a simple design. The static friction is generated between the at least second component and a region of the implant, in particular directly, in the direction of the distal end, on the proximal end, in the insertion device. The material can be any material considered reasonable by a person skilled in the art, such as a polymer and, in particular, a material selected from the group comprising polyamide, polyester, polyether block amide, silicone, polyurethane. As a result, the at least second component can be designed having low weight in particular. Particularly reliable positioning of the implant in the insertion device can be advantageously achieved due to the high static friction thereof when the material is a polyether block amide such as PEBAX from the company Arkema, for example. All hardnesses can be used. Basically, the material of the at least second component can also have elastic and/or resilient properties. It would also be possible for the at least second component to comprise at least one resilient element, such as a compression spring, for generating a clamping effect.

Furthermore, the first component comprises a material that is harder than the material of the at least second component, thereby enabling the first component to withstand high forces particularly well, in particular radial forces of the second component and/or the implant. Preferably, the material is a material, in particular, selected from the group comprising a plastic such as polycarbonate, polyetheretherketone PEEK, perfluoroethylene propylene, high density polyethylene, polytetrafluoroethylene, polyamide, —preferably a hard plastic, in particular polycarbonate, polyetheretherketone PEEK, polyamide, —a metal, a ceramic, a hard rubber or a glass. Advantageously, the material of the first component is a metal, preferably a stainless steel, thereby enabling a material to be used that is resistant to and compatible with aggressive media such as bodily fluids.

In a preferred embodiment, the first component and/or the at least second component have a monolayer design. Materials can be used for the first component such as, in particular, a plastic (e.g. polycarbonate, polyetheretherketone PEEK, polyamide) or a metal (steel), and materials can be used for the at least second component such as, in particular, polyurethanes, silicones, rubber, polyamides, polyester or polyether block amide, preferably such as PEBAX.

In an alternative embodiment, the first component and/or the at least second component have a multilayer design or a so-called multilayer, co-extruded design. In this case, the first component and/or the at least second component have at least two layers which are disposed one behind the other in the radial direction, or one on top of the other. For the first component, a material having low friction is selected, for instance, for a radially outer layer or an outer layer, and a material having higher friction is selected for a radially inner layer or an inner layer. As a result, the first component can be moved nearly frictionlessly in the insertion device or the outer shaft thereof, and the implant can be affixed in the first component with high holding force. A radially inner layer or an inner layer of the at least second component is preferably selected from a material having low friction, and a radially outer layer or an outer layer is selected from a material having higher friction. As a result, the at least second component can be moved easily on the inner shaft of the insertion device, for example, and, simultaneously, the high friction between the outer layer of the at least second component and the implant can be attained.

The layer having lower friction preferably has a material selected from the group comprising perfluoroethylene propylene (FEP), high density polyethylene (HDPE), polytetrafluorethylene (PTFE, Teflon) or hydrophobically/hydrophilically coated polyamides (PA), in particular PA-6, -6.6, -6.10, -6.12, -11, -12. The layer having higher friction preferably has a material selected from the group comprising polyamide, polyester, polyether block amide (PEBAX), silicone, polyurethane, (PUR), rubber. A further, middle layer can be provided to ensure good contacting of the two layers.

This middle layer is preferably made of a material which is suitable for use as a primer, i.e. it can create adhesion between the outer layer and the inner layer. The middle layer preferably comprises the material linear low density polyethylene (LLDP). Furthermore, a coating can be applied to the relevant layer to reduce friction. This coating can be hydrophobic or hydrophilic and can be made of any material considered reasonable by a person skilled in the art.

In a further embodiment of the invention, the first component and/or the at least second component comprise a passage for receiving one of the insertion elements. This results in a compact configuration which stabilizes and protects the insertion element. If the insertion device is a catheter, the applicable insertion element can be an inner shaft of the catheter.

It is furthermore advantageous for the first component to be disposed on the proximal end of the clamping unit, and for the at least second component to be disposed on the distal end of the clamping unit. As a result, it is easy to place the implant in the clamping unit and release the implant. The at least second component or the plug connector is therefore disposed after the first component or the socket in a direction from the proximal end toward the distal end of the clamping unit or the insertion device. It should therefore be possible to adjust an axial distance to be as small as possible in order to prevent inhomogeneities in the support of the implant, which could impair the stability and functionality of the implant. This distance is dependent on a design of the implant that is used and is selected by a person skilled in the art on the basis of his technical expertise, of course.

The clamping unit and the insertion device can be designed to be particularly comfortable and easy to operate by disposing the first component and/or the at least second component on one of the insertion elements in an axially fixed manner. In particular, the first component and/or the at least second component can therefore be operated and/or moved by way of the insertion element, in particular being retracted for and/or after release of the implant, thereby making it possible to advantageously operate the release device in a controlled manner. If the insertion device is a catheter, the insertion element is preferably the inner shaft. In addition, the implant can be held particularly captively in the clamping unit when an inner diameter of the first component is wider, by a maximum of 0.2 mm, than an outer diameter of a proximal end of the implant in the compressed state. The compressed state of the implant is the state in which the implant or the proximal end thereof is compressed immediately before placement on the first component and, in particular, insertion into the cavity of the first component. In particular, the implant is already on the inner shaft and is placed and/or crimped radially around the second component. In principle, the difference in diameter could also be less, although it must be ensured that the implant can be clamped in a stress-free manner, in particular without incurring damage due to irreversible deformations, for example.

Furthermore, one end of the first component can be widened and/or expanded relative to the other end with respect to the extension and/or diameter thereof. As a result, the implant can be easily inserted into the first component. After the inserted end of the implant stops against a radial inner surface of the first component, the implant is affixed upon further insertion via compression of an extension or a diameter of the implant by means of the inner surface which is beveled in the axial direction. The widening and/or expanding can be carried out using any method considered applicable by a person skilled in the art, and/or is dependent on a material of the first component in particular. Preferably, the distal end is expanded, and therefore the sleeve region or the distal end thereof is likewise expanded. Basically, the first component could also be elastic and the end could be elastically widened in the clamped state.

In an alternative embodiment, the first component and/or the at least second component have a conical contour for interaction with the respective other component and/or the implant. This results in a compact design of the insertion device. Preferably, the first component comprises a cavity which tapers toward the proximal end, and/or the at least second component comprises a portion which tapers toward the proximal end, such as a truncated cone.

According to a further aspect of the invention, an insertion device is provided for inserting a medical implant which can be released by way of a relative motion between a first and a second insertion element, comprising a release device for releasing the medical implant, comprising a clamping unit for clamping the implant in the insertion device, having a proximal end which is distant from a distal end of the insertion device in the state of use, and a distal end which faces the distal end of the insertion device in the state of use, wherein the clamping unit comprises a first component and at least one second component, which clamp the implant therebetween in the clamped state.

By way of the embodiment according to the invention, an insertion device can be provided, in which the implant is securely held or is securely fastened on the inner shaft of the insertion device. The clamping unit furthermore makes it possible to achieve a compact and simple design of the insertion device. In addition, the implant can be easily mounted on the insertion device or the catheter. Moreover, release of the implant is reliable and rapid. Furthermore, it is possible to eliminate the risk of deformation of the implant and resulting blockage of the insertion device, which occur with devices according to the prior art, which utilize hooks and eyes. The insertion device can be a catheter, which is favorable. Particularly advantageously, the insertion device can be used to install and release a prosthesis, a heart valve or a stent.

It is also provided that the insertion device comprises a stopper which limits a motion of the implant in the direction of a proximal end of the insertion device. Such a motion would disadvantageously result in blockage of the implant. In a preferred development, the clamping unit comprises a stopper, thereby clearly defining a position of the clamping unit during movement of the outer insertion element in the direction of a proximal end of the insertion device or the relative motion of the two insertion elements. Furthermore, the stopper can be connected to one of the components of the clamping unit, thereby effectively preventing the clamping unit from becoming displaced relative to the stopper. Any type of connection considered reasonable by a person skilled in the art can be used, such as a frictional connection, a form-fit connection, or a bonded connection. Particularly preferably, the first component of the clamping unit is designed as one piece with the stopper, thereby permitting the system to have a very stable design. In this context, "as one piece" is intended to mean that the stopper and the first component are formed by the same component and/or that separating them would result in loss of functionality of at least one of the components.

According to an advantageous embodiment, the implant can be a self-expanding implant, thereby enabling it to advantageously support the connection to the first component by way of the inherent radial force thereof. Since the implant is self-expanding, an additional expanding means can be omitted. It is thereby possible, advantageously, to save space and assembly expense therefore. It is thereby also possible to simplify the design of the insertion device. It would also be possible, in principle, to use a balloon-expandable implant, however. To this end, the insertion device would have to be adapted accordingly, however, which a person skilled in the art achieves, of course, due to his technical expertise. Particularly preferably, the implant is designed without fastening elements, thereby enabling the implant to be shorted compared to implants according to the prior art. This has a positive effect for patients in particular. The insertion device can therefore also be designed without fastening elements. As a result, connection of fastening elements such as hooks and eyes, which would be required otherwise, is omitted from the mounting of the implant on the insertion device, thereby also reducing waste resulting from faulty assembly, thereby reducing costs. This results in time savings, in particular, in the preparation of the insertion device in the preparation laboratory. Moreover, the step of releasing the connection between hooks and eyes during the implantation procedure, which is often associated with problems in the prior art, is omitted. In addition, the implant can be positioned highly precisely instead of utilizing hooks and eyes as in the prior art.

In addition, a method is provided for clamping a medical implant by way of a clamping unit of a release device in an insertion device, in which the implant is released by way of a relative motion between a first and a second insertion element. The clamping unit has a proximal end which is distant from a distal end of the insertion device in the state of use, and a distal end which faces the distal end of the insertion device in the state of use. The method comprises at least the following steps: Place the implant on an insertion element, and place at least a part of the implant over at least one second component of the clamping unit, so that at least one proximal end of the implant is disposed proximal to the second component; bend at least one proximal end of the implant radially in the direction of an inner axis of the implant; insert at least the proximal bent end of the implant into a first component of the clamping unit, so that at least one region of the implant rests radially against at least one region of an outer surface of the second component, and place the clamping unit comprising the implant in at least one insertion element.

By way of the embodiment according to the invention, a method can be achieved which enables the implant to be placed and fastened in the insertion device in a manner that is user-friendly, precise, reliable and rapid. An implant mounted in such a manner can also be released in a manner that is user-friendly, precise, reliable and rapid. The implant is placed on the insertion element preferably by way of fastening and, in particular, a crimping process. Furthermore, before the implant is placed, the proximal end thereof can be bent radially outwardly in order to overcome the radial extension of the second component. After the placement/fastening/crimping of the implant or placement of the part of the implant and overcoming the second component, the proximal end, at least, of the implant can be bent radially in the direction of the inner axis of the implant. It would also be possible for the second component to be captively held in the insertion device by the second component resting radially against the implant via at least one region of the outer surface. In this context, "one region of the implant" is intended to mean at least one region of the implant that rests directly against the proximal end of the implant in the direction of the distal end. Basically, the region could also be the proximal end and/or a region in a center of the implant.

Preferably the region of the implant rests radially against the entire outer surface of the at least second component. In this case, the expression "slide at least a portion of the implant over at least one second component of the clamping unit" is intended to mean that the entire implant is not slid over the second component, but rather only a portion thereof and, in particular, at least the proximal end. The second component is therefore disposed radially in the implant.

Turning now to the figures by way of additional illustration of invention embodiments, elements that are functionally identical or similar-acting are labeled using the same reference marks in the figures. The figures are schematic depictions of an example embodiment of the invention. They do not depict specific parameters of all embodiments or features of the invention. Furthermore, the figures merely show typical embodiments of the invention and should not limit the invention to the embodiments shown. Still further, some aspects of various invention embodiments are shown in various of the figures that are not discussed herein, and it will be appreciated that failure to discuss those features does not limit the scope of the invention embodiments which may include illustrated features.

FIG. 1 shows a longitudinal view through a favorable embodiment of a release device 100, according to the invention, of an insertion device 110 which is only partially depicted. The insertion device 110 is a catheter, for example, comprising a shaft region 50 having two coaxially disposed insertion elements 52, 54, e.g. an inner shaft (insertion element 52) and, enclosing same, an outer shaft (insertion element 54) which can be enclosed by an outer sleeve which is not shown. In the state of use by an operator, i.e. during fastening of an implant 105 to the release device 100 or during implantation, the insertion device 110 faces an operator by way of the proximal end 115 thereof. The implant 105 is placed at the distal end 120 of the shaft region 50 between the inner shaft and the outer shaft, and is intended for release at the implantation site in the animal body or human body (see FIG. 5).

The release device 100 serves to release the medical implant 105 from the insertion device 110. The implant 105 is disposed at an end 120 of the shaft region 50 facing away from the user, e.g. in the vicinity of a catheter tip (see FIG. 5). The implant 105 is placed around the inner insertion element 52, for example, and is released by way of a relative motion between the first and the second insertion elements 52, 54.

The release device 100 comprises a clamping unit 10 for clamping the implant 105 in the insertion device 110. In addition, the clamping unit 10 has a proximal end 12 which is distant from the distal end 120 of the insertion device 110 in the state of use, and a distal end 14 which faces the distal end 120 of the insertion device 110 in the state of use. Furthermore, the clamping unit 10 comprises a first component 16 and a second component 18, which, in the clamped state, clamp the implant 105 therebetween in the clamping unit 10 in a longitudinal or axial direction 34 and a transversal direction 36. In the clamped state, a form-fit connection between the first component 16 and the implant 105, and friction between the second component 18 and the implant 105 hold the implant in position.

To establish the form-fit connection with the implant 105, the first component 16 is designed as a generally cup-shaped socket 20. A cylindrical portion of the socket 20, which is disposed in the direction of the distal end 14 of the clamping unit 10, is a sleeve region 38 which, in the clamped state, encloses a proximal end 106 of the implant 105 in a circumferential direction 40 and clamps it in the transverse direction 36 and the radial direction 42. The sleeve region 38 forms a cavity 44 in which the proximal end 106 of the implant 105 can be accommodated and disposed, and in which it is disposed in the clamped state. A wall 46 extending in the radial direction 42 is integrally formed on a region of the first component 16 disposed in the direction of the proximal end 12 of the clamping unit 10 to thereby close an end of the socket 20.

The second component 18 is formed by a cylindrical component and is a plug connector 22 which can be disposed within an interior region of the implant 105 or is disposed in the implant 105 in the clamped state. One region 108 of the implant 105 rests radially against a region 30 of an outer surface 32, which is the entire radial outer surface 32 in this case, of the second component 18 or the plug connector 22. By way of this design, the region 108 of the implant 105 is pressed in the transverse direction 36 and the radial direction 42 against the insertion element 54 or the outer shaft, and is clamped between it and the plug connector 22. The first component 16 is disposed at the proximal end 12 and the second component 18 is disposed at the distal end 14 of the clamping unit 10. The second component 18 or the plug connector 22 is therefore disposed behind the first component 16 or the socket 20 in an axial direction 34 from the proximal end 12 to the distal end 14 of the clamping unit 10 or the insertion device 110. The components 16 and 18 cooperate in this manner to provide clamping or holding power on the implant 105. Both components 16, 18 are fixedly disposed in the axial direction 34 on the insertion element 52 or the inner shaft, thereby enabling them to move with the insertion element 52. To this end, the first component 16 and the second component 18 each comprise a passage 24 for the insertion element 52 or the inner shaft. Both the first and second components 16 and 18 are fixedly attached to the inner shaft 52 so that they move together relative to one another as the inner shaft 52 is moved.

To ensure the required adhesion between the implant 105 and the second component 18 or the plug connector 22, in particular to hold the implant 105 in position in the insertion device 110 in the clamped state, it is made of a monolayer-design polymer (e.g., PEBAX from the company Arkema) having high static friction. The first component 16, however, is made of a material that is harder than the material of the second component 18. As a result, the socket 20 can be moved easily in the insertion element 54 (outer shaft). The material of the first component 16 is a hard plastic, for example, such as polycarbonate. As an alternative it would also be possible to produce the component 16 with a so-called multilayer, co-extruded design having an outer layer and an inner layer (not shown). In this case, the outer layer would be made of a material having low friction (e.g., PC), and the inner layer would be made of a material having high friction (e.g., PEBAX). The form-fit connection between the first component and the proximal end of the implant can be supported by the high friction of the material of the inner layer.

Figure 2:
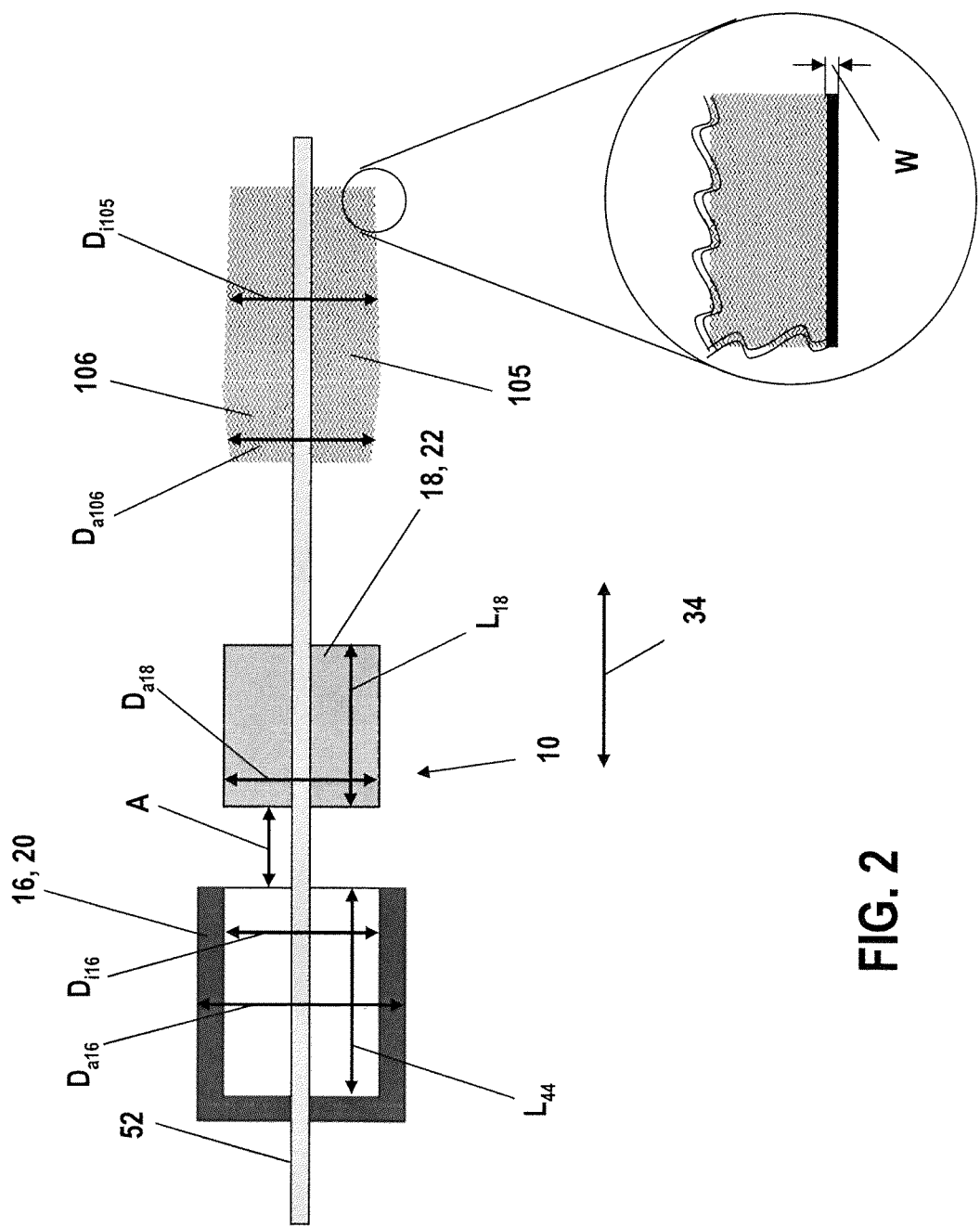
FIG. 2 a schematic depiction of two components of the release device and the implant shown in FIG. 1.

FIG. 2 shows a schematic depiction of the two components 16, 18 of the release device 100, and the implant 105. The first and the second component 16, 18 each have a substantially round cross section (not shown in detail). An inner diameter $D_{i16}$ of the first component 16 or the cavity 44 thereof is matched to a contour or an outer diameter of the implant 105 that is used, and is therefore dependent on the dimensions and properties thereof. Basically it should be as small as possible, e.g. between 0.1 mm to a maximum of 0.2 mm wider than an outer diameter $D_{a106}$ of the proximal end 106 of the implant 105 in the compressed state of the crimped implant 105 before insertion thereof into the cavity 44 of the first component 16 (see FIG. 4). A length $L_{44}$ of the cavity 44 is likewise dependent on the implant 105 that is used, and can be 5 mm to 10 mm, for example. Furthermore, an outer diameter $D_{a16}$ of the first component 16 is matched to dimensions of the insertion device 110, such as an inner diameter $D_{i54}$ of the insertion element 54 or the outer shaft (see FIG. 1). For example, an outer diameter $D_{a16}$ of the first component 16 can be the inner diameter $D_{i54}$ of the outer shaft 54 minus 0.2 mm or some other small tolerance distance, thereby enabling the first component 16 to be disposed in the insertion device 110 with a radial gap of 0.1 mm or some other small distance in the installed state.

In some embodiments, an outer diameter $D_{a18}$ of the second component 18 is reduced relative to the inner diameter $D_{i54}$ of the outer shaft 54 by twice the wall thickness W of the implant 105 that is used and is therefore dependent on dimensions such as an inner diameter $D_{i105}$, and on properties of the implant 105. A length $L_{18}$ of the second component 18 or the plug connector 22 can be 5 mm, for example. An axial distance A between the first component 16 and the second component 18 is dependent on the dimensions and properties of the implant 105 and should be as short as possible. It can be 1 mm to 5 mm, for example.

Figure 3:
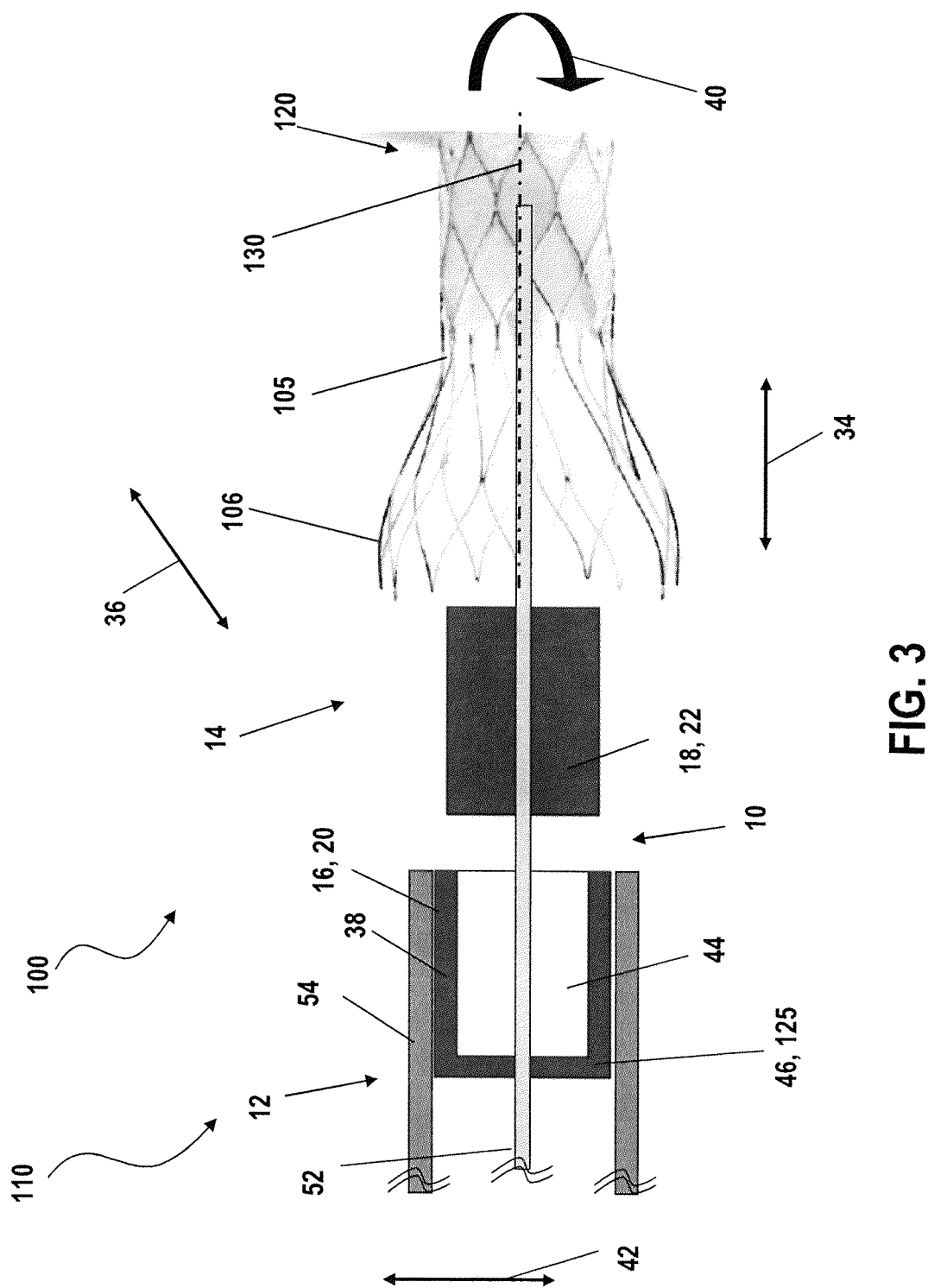
FIG. 3 the release device and the implant shown in FIG. 1 in a state before the implant is placed in the insertion device.

FIG. 3 shows the insertion device 110 before the implant 105 is placed in the clamping unit 10. To this end, the outer insertion element 54 would be displaced in the direction of the proximal end 115 of the insertion device 110 until the first component 16 is exposed at an edge of the outer insertion element 54 which points toward the distal end 120 of the insertion device 110. The first and the second components 16, 18 can be preinstalled in an insertion device 110, e.g. by a manufacturer, or they can be installed in the catheter laboratory shortly before the implant 105 is installed. The insertion device 110 comprises a stopper 125 for limiting the motion of the implant 105 in the direction of the proximal end 115 of the insertion device 110 during installation. This stopper 125 is formed by the wall 46 and is therefore designed as one piece with the first component 16 of the clamping unit 10. The implant 105, e.g. a stent or an artificial heart valve implant, is self-expanding and comprises no fastening elements, i.e. it is designed without hooks or eyes, for example.

Figure 4:
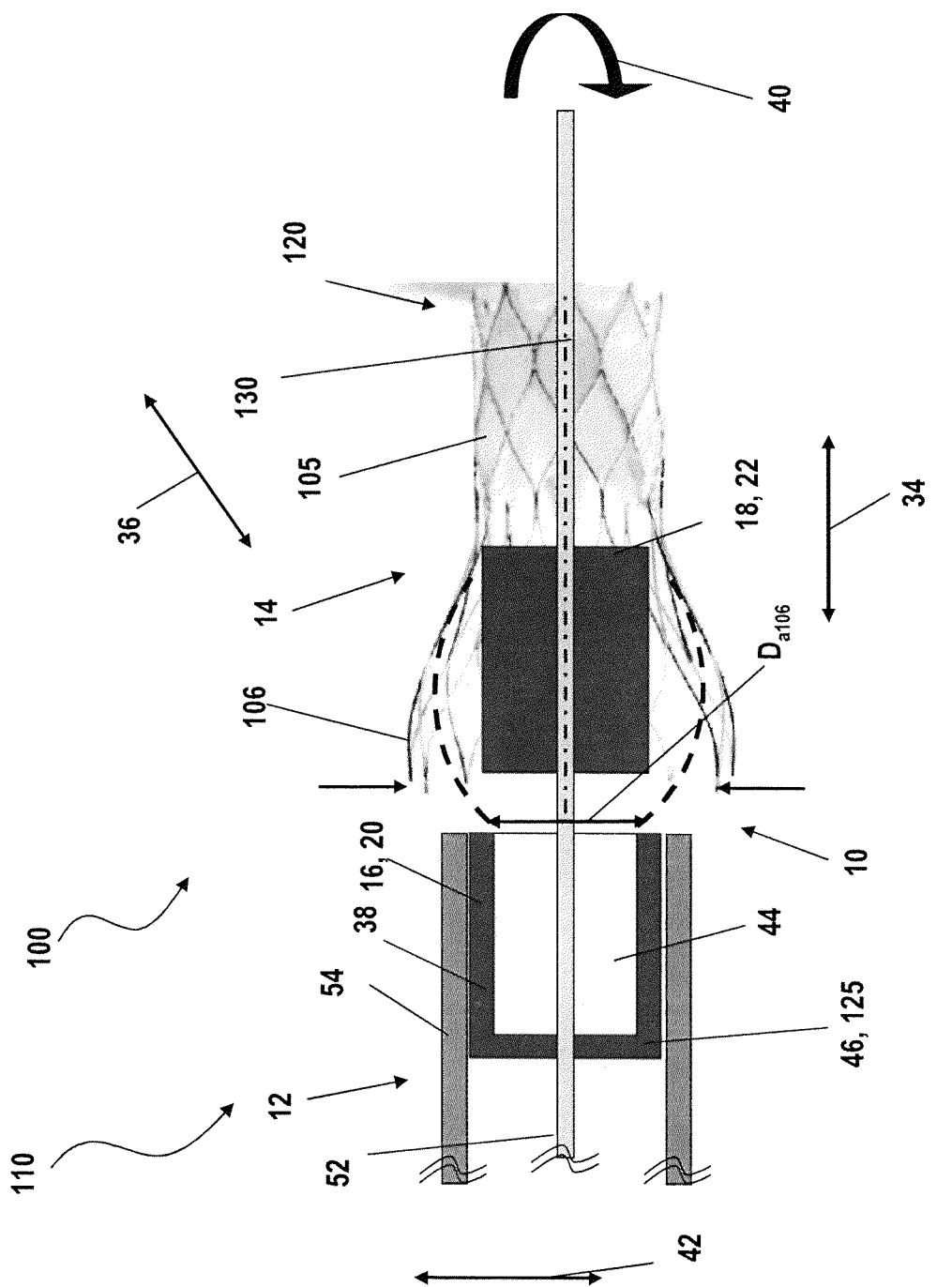
FIG. 4 the release device and the implant shown in FIG. 1 after the implant is placed and bent at the insertion device.
Figure 5:
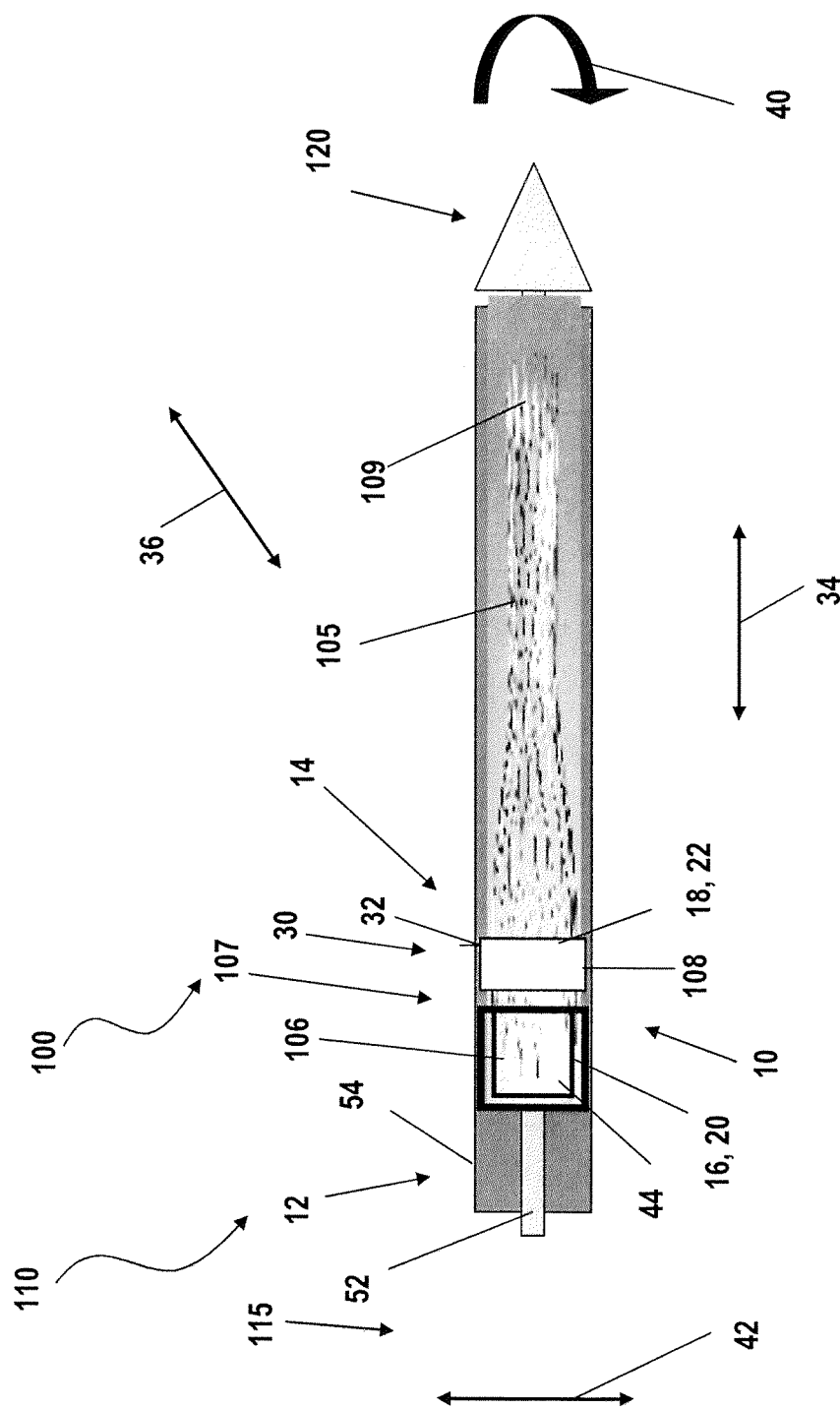
FIG. 5 a section through a distal end of the insertion device shown in FIG. 1 comprising the release device disposed therein, with the implant in place, and FIG. 6 an alternative release device and an implant in a state before the implant is placed in an insertion device.

A method for clamping the implant 105 by way of the clamping unit 10 is described in the following with reference to FIGS. 4 and 5. In a first step, the implant 105 is placed. The entire implant 105 is slid over the inner insertion element 52, and a portion 107 of the implant 105 is slid over the second component 18 of the clamping unit 10, and therefore at least the proximal end 106 of the implant 105 is disposed proximal to the second component 18, axially between the first and the second components 16, 18 (see FIG. 4). Once the implant 105 has been placed, it is fastened to the inner insertion element 52 by way of crimping. FIG. 4 likewise shows that, in a subsequent, second step, the proximal end 106 of the implant 105 is bent radially in the direction of an inner axis 130 of the implant 105 (see arrows), whereby the proximal end 106 of the implant 105 assumes the position depicted schematically using dashed lines. In a third step, the implant 105, which has been bent in this manner, or the proximally bent end 106 thereof is inserted from the direction of the distal end 14 into the cavity 44 of the first component 16 of the clamping unit 10. The implant 105 is placed in such a way that the region 108 of the implant 105 rests radially against the region 30 of the outer surface 32 of the second component 18, in particular against the entire radial outer surface 32 (see FIG. 5). The portion 107 is the proximal end 106 of the implant 105 and the portion 108 to be connected distally thereto. The implant 105 is now held in position on the inner insertion element 52 by way of the form-fit connection between the first component 16 and the implant 105. In a final step, the outer insertion element 54 is slid over the clamping unit 10, thereby placing the clamping unit 10 comprising the implant 105 in the insertion element 54 (see FIG. 5). The implant 105 is now held in position by way of the form-fit connection between the first component 16 and the implant 105 and by way of the interaction of the implant 105 with an inner surface of the outer insertion element 54. This secure position is supported further by way of the static friction between the second component 18 and the implant 105 when the clamping unit 10 and the implant 105 move in the outer insertion element 54, thereby reliably preventing the implant 105 from sliding out.

In order to implant the implant 105 in the body, the insertion device 110 prepared in this manner is introduced into the body. By moving the outer insertion element 54 in the direction of the proximal end 115 of the insertion device 110, when a distal end 109 of the implant 105 is exposed, it opens and is positioned first due to the self-expanding capability thereof. When the outer shaft and the inner shaft comprising the first and second components 16, 18 fastened thereon are retracted, the proximal end 106 of the implant 105 is also released. As a result, the proximal end 106 of the implant 105 also opens due to the radial force thereof. Next, the release device 100 or the clamping unit 10 comprising the inner shaft is retracted into the outer shaft, and the insertion device 110 is removed from the body. The implant 105 remains permanently positioned in the body (not shown).

Figure 6:
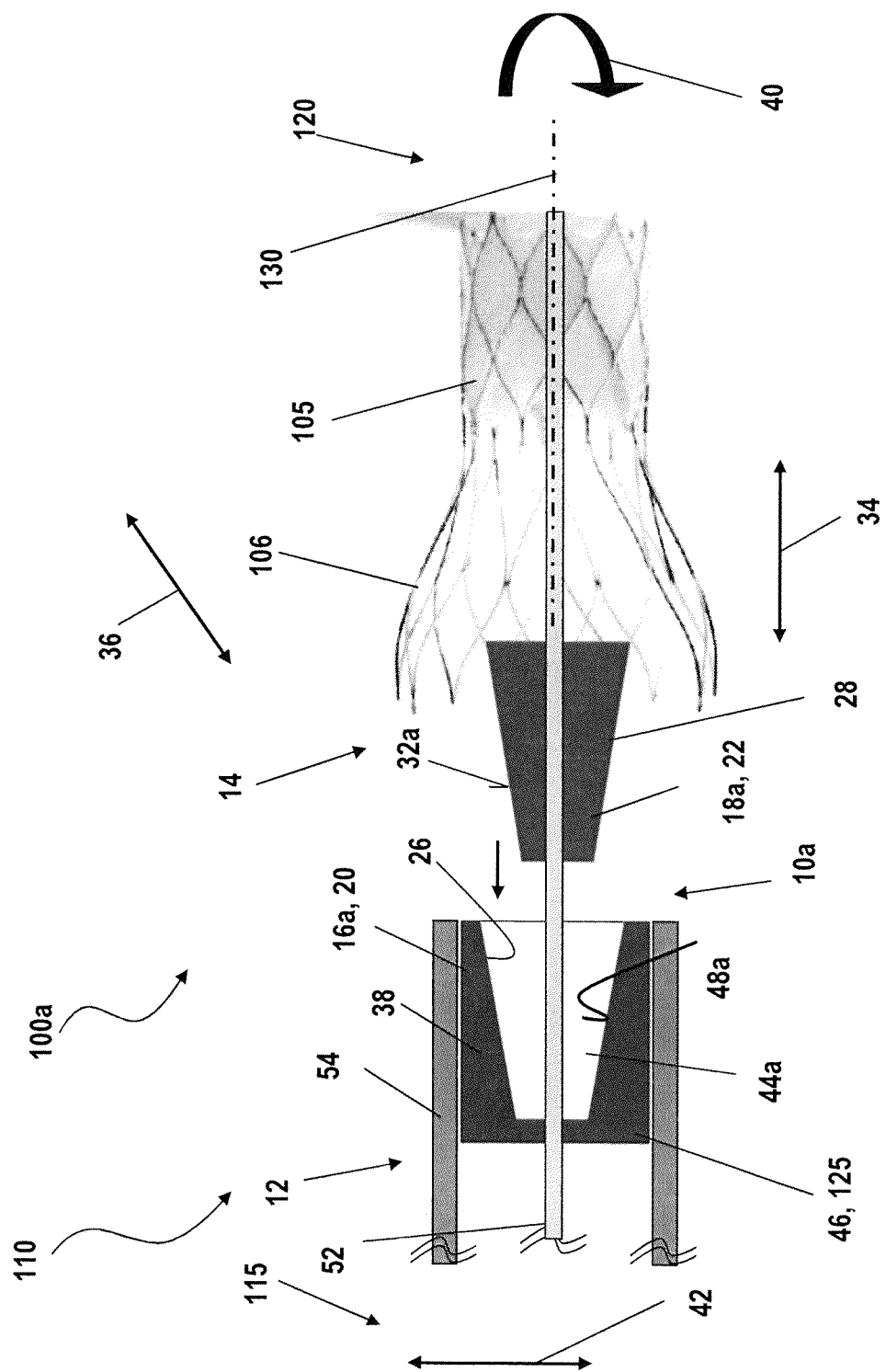

An alternative embodiment of the release device 100a is shown in FIG. 6. Components, features, and functions that are essentially the same are labeled using the same reference marks. However, the letter "a" is appended to the reference marks of the components which deviate in the embodiment shown in FIG. 6, to differentiate the embodiment shown in FIG. 6 from that shown in FIGS. 1 to 5. The description that follows is limited mainly to the differences from the embodiment presented in FIGS. 1 through 5, and reference can be made to the description of the embodiment shown in FIGS. 1 through 5 with regard for the components, features, and functions that remain the same.

The release device 100a in FIG. 6 differs from the release device 100 in FIGS. 1 to 5 in that a first component 16a and a second component 18a of a clamping unit 10a each have a cooperating truncated conical contour 26, 28 for interaction with the respective other component 16a, 18a and an implant 105. The conical contour 26 of the first component 16a is formed by two radial inner surfaces 48a of a cavity 44a of the first component 16a, which extend toward one another in the direction of a proximal end 12 of the clamping unit 10a. The second component 18a has, as a conical contour 28, two outer surfaces 32a which extend toward one another in the direction proximal end 12, which are designed to correspond to the two inner surfaces 48a of the first component 16a. In this embodiment, the second component 18a is disposed on an inner insertion element 52 of an insertion device 110 such that it is displaceable in the axial direction 34, and can be inserted into the cavity 44a of the first component 16a from the direction of a distal end 14 of the clamping unit 10a. As a result, the implant 105 or a proximal end 106 of the implant 105 is clamped between the inner surfaces 48a of the first component 16a and the outer surfaces 32a of the second component 18a, and the implant 105 is also held in the cavity 44a by the second component 18a. Due to the absence of a connection between the second component 18a and the inner insertion element 52, the insertion element 52 must comprise a carry-along element, which is not shown in greater detail, to enable the second component 18a to be removed from the body after the implant 105 has been released in the body. This carry-along element could be formed by a catheter tip if the insertion unit is designed as a catheter.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release device for releasing a medical self-expanding implant from an insertion device, in the case of which the self-expanding implant can be released by way of a relative motion between inner and outer shafts, comprising a clamping unit for clamping the self-expanding implant in the insertion device, having a proximal end which is distant from a distal end of the insertion device, and a clamping unit distal end which faces the distal end of the insertion device, wherein the clamping unit comprises a cup-shaped socket that accepts a proximal end of the self-expanding implant, wherein the cup-shaped socket is configured to withstand radial forces of the self-expanding implant, and a plug connector is fixed on the inner shaft that presses the self-expanding implant against the outer shaft and is separated by an axial distance from the cup-shaped socket, wherein the plug connector and the cup-shaped socket cooperate to clamp the self-expanding implant there between in a clamped state when the self-expanding implant is within the outer shaft and to release the self-expanding implant via proximal retraction of the outer shaft to release a distal end of the self-expanding implant followed by retraction of the inner and outer shafts to release a proximal end of the self-expanding implant.

2. The release device according to claim 1, wherein, in the clamped state, a form-fit connection is defined between the cup-shaped socket and the self-expanding implant to hold the self-expanding implant in position, or friction between the plug connector and the self-expanding implant holds the self-expanding implant in position.

3. The release device according to claim 1, wherein the plug comprises a material having sufficient static friction to hold the self-expanding implant in position in the clamped state and during the proximal retraction of the outer shaft.

4. The release device according to claim 3, wherein the material is selected from the group consisting of polyamide, polyester, polyether block amide, silicone, polyurethane.

5. The release device according to claim 3, wherein the cup-shaped socket comprises a material that is harder than the material of the plug connector and is a material selected from the group consisting of a plastic, perfluoroethylene propylene, high density polyethylene, polytetrafluoroethylene, poly-amide, a metal, a ceramic, a rubber or a glass.

6. The release device according to claim 5, wherein the material of the cup-shaped socket is a metal.

7. The release device according to claim 1, wherein the cup-shaped socket and the plug connector each have a passage for receiving the inner shaft.

8. The release device according to claim 1, wherein the cup-shaped socket is disposed on the proximal end of the clamping unit, and the plug connector is disposed on the distal end of the clamping unit.

9. The release device according to claim 1, wherein an inner diameter (Di16) of the cup-shaped socket is wider by a maximum of 0.2 mm than an outer diameter (Da106) of a proximal end of the self-expanding implant in when the self-expanding implant is in a compressed state within the outer shaft.

10. The release device according to claim 1, wherein one or both of the cup-shaped socket and the plug connector have a conical contour.

11. The release device according to claim 1, further comprising a stopper formed as a proximal portion of the cup-shaped socket.

12. The release device according to claim 1, wherein the self-expanding implant lacks fastening elements.

13. The release device of claim 1, wherein the cup-shaped socket comprises a material that is harder than a material of the plug connector.

14. The release device of claim 13, wherein the material of the cup-shaped socket is selected from the group consisting of a polyehteretherketone (PEEK), perfluoroethylene propylene, high density polyethylene, polytetrafluorethylene, polyamide, a metal, a ceramic, a hard rubber or a glass.

15. The release device of claim 14, wherein the material of the plug connector is an elastic or resilient polyether block amide.

16. The release device of claim 1, wherein the plug connector comprises a multilayer material with an inner layer of low friction material selected from the group consisting of perfluoroethylene propylene (FEP), high density polyethylene (HDPE), polytetrafluoroethylene (PTFE, Teflon) or hydrophobically/hydrophilically coated polyamides (PA), including PA-6, -6.6, -6.10, -6.12, -11, -12, and an outer layer of high friction material selected from the group consisting of polyamide, polyester, polyether block amide (PEBAX), silicone, polyurethane (PUR), and rubber.

* * * * *